(12) United States Patent
Pacheco et al.

(10) Patent No.: US 7,816,409 B2
(45) Date of Patent: Oct. 19, 2010

(54) STABLE PHARMACEUTICAL COMPOSITION OF FLUOROETHER COMPOUND FOR ANESTHETIC USE METHOD FOR STABILIZING A FLUOROETHER COMPOUND, USE OF STABILIZER AGENT FOR PRECLUDING THE DEGRADATION OF A FLUOROETHER COMPOUND

(75) Inventors: Ogari Pacheco, Itapira (BR); Elisa Russo, Itapira (BR); Valter Russo, Itapira (BR); José Antônio Martins, Itapira (BR); Maria Alice Bockelmann, Campinas (BR); Simone Rosatto, Itapira (BR)

(73) Assignee: Cristalia Productos Quimicos Farmaceuticos LTDA, Itapira, SP (BR)

( * ) Notice: Subject to any disclaimer, the term of this patent is extended or adjusted under 35 U.S.C. 154(b) by 1282 days.

(21) Appl. No.: 10/566,466

(22) PCT Filed: Aug. 20, 2004

(86) PCT No.: PCT/BR2004/000156

§ 371 (c)(1),
(2), (4) Date: Jan. 31, 2006

(87) PCT Pub. No.: WO2005/023175

PCT Pub. Date: Mar. 17, 2005

(65) Prior Publication Data

US 2006/0228383 A1 Oct. 12, 2006

(30) Foreign Application Priority Data

Sep. 10, 2003 (BR) .................................. 0303489
Jul. 29, 2004 (BR) ..................................... 07698

(51) Int. Cl.
*A61K 31/08* (2006.01)
*A01N 31/14* (2006.01)
*C07C 43/00* (2006.01)

(52) U.S. Cl. ...................... 514/722; 514/715; 514/816; 568/683

(58) Field of Classification Search ................. 424/400; 514/722, 715, 816; 568/683
See application file for complete search history.

(56) References Cited

U.S. PATENT DOCUMENTS

| | | | | |
|---|---|---|---|---|
| 3,216,897 A | * | 11/1965 | Krantz, Jr. ................... | 514/722 |
| 5,990,176 A | * | 11/1999 | Bieniarz et al. ............. | 514/722 |
| 6,074,668 A | | 6/2000 | Flament-Garcia et al. | |
| 6,271,422 B1 | * | 8/2001 | Bieniarz et al. ............. | 568/683 |

FOREIGN PATENT DOCUMENTS

| | | | |
|---|---|---|---|
| EP | 1663186 | * | 6/2007 |
| WO | WO-98/32430 A1 | | 7/1998 |
| WO | WO-99/34762 A1 | | 7/1999 |
| WO | WO-03/018102 A2 | | 3/2003 |
| WO | WO-03/030862 A2 | | 4/2003 |
| WO | WO-2005/023175 A2 | | 3/2005 |

OTHER PUBLICATIONS

Yang, et al., Gaoxiang Yi Xue Ke Xue Zu Zhi, 1990, 6(3), p. 127-30 (abstract).*
Brown et al., Environmental Health Perspectives, 1977, 21, p. 185-188.*
R.F. Wallin et al., Abstract of "Anesth Analg.", vol. 54, No. 6, Nov.-Dec. 1975, pp. 758-766.

* cited by examiner

*Primary Examiner*—Michael G Hartley
*Assistant Examiner*—Leah Schlientz
(74) *Attorney, Agent, or Firm*—Birch, Stewart, Kolasch & Birch, LLP (57) ABSTRACT

The present invention has as objective the stabilization of a fluoroether compound against degradation by acid substances. The stabilizers proposed are selected among propylene glycol, polyethylene glycol, hexylene glycol, 1,3-butylene glycol and a saturated cyclic alcohol preferably menthol and are used for preparing stable pharmaceutical compositions of a fluoroether compound. Method for stabilizing a fluoroether compound and use of stabilizers agents for precluding the degradation of a fluoroether are also described.

27 Claims, 7 Drawing Sheets

STABLE PHARMACEUTICAL COMPOSITION OF FLUOROETHER COMPOUND FOR ANESTHETIC USE METHOD FOR STABILIZING A FLUOROETHER COMPOUND, USE OF STABILIZER AGENT FOR PRECLUDING THE DEGRADATION OF A FLUOROETHER COMPOUND

The present invention has as objective the stabilization of a fluoroether compound against degradation occasioned by acid substances.

Particularly, the present invention refers to stabilization of fluoroether compounds having anesthetic properties and stabilized pharmaceutical compositions of fluoroether compounds for use in anesthesia. The stabilizers employed are selected from the suitable pharmaceutical compounds and are used in the preparation of stabilized pharmaceutical compositions. The present invention also describes, a method for precluding the degradation of a fluoroether compound and use of stabilizer agents for precluding the degradation of a fluoroether compound, said degradation being occasioned by acid substances.

Fluoroether compounds, with anesthetic properties, related to the present invention, include sevoflurane, desflurane, isoflurane, enflurane and methoxiflurane. Among these fluoroether compounds the present invention has particular application to sevoflurane.

Acid substances according to the present invention scope refer to substances that present acid character and in special to metallic impurities of acid character which in diverse conditions can contact with a fluoroether compound such as sevoflurane.

The decomposition of fluoroether compounds is a phenomenon few common, being generally originated from combination with substances presenting a reactive profile or behavior in relation to these compounds.

Among the decomposition types, it is known the degradation of the fluoroether compound sevoflurane occasioned by $CO_2$ (carbon dioxide) absorbent agents usually employed in the vaporization circuit of this product. These $CO_2$ absorbents are relatively strong bases as the case of "soda lime" (composed of calcium hydroxide, sodium hydroxide and potassium hydroxide) and of "baralime" (composed of calcium hydroxide and barium hydroxide), both absorbents have water content ranging from 14% to 19% to provide effective and efficient absorption of $CO_2$. The mechanism of degradation involves the removal of an acid proton from sevoflurane by these bases with formation of an olefin known as Compound A (2-(fluoromethoxy)-1,1,3,3,3-pentafluoro-propene) which is subject of intense debate due to its possible nefrotoxicity in humans [*Royal College Of Anesthetics Newsletter*—January 2000, Issue no. 50 pg. 287-289].

In order to avoid this kind of degradation by the usual $CO_2$ absorbents, the use of sevoflurane in open circuits and employing low flux vaporization became the usual recommendation to specialists and anesthesiologists for using this kind of anesthetic agent.

Also, the degradation of sevoflurane with the possible formation of Compound A in significant amounts motivated the development of $CO_2$ absorbents that could avoid this kind of degradation as is the case of AMSORB® [J. M. Murray et al, "Amsorb—a new carbon dioxide absorbent for use in anesthetic breathing systems"—*Anesthesiology* 1999].

In addition to the mechanism of degradation of sevoflurane in presence of $CO_2$ absorbents, with high probability of occurrence related only with vaporization circuits of the product in anesthetic procedures, a second mechanism of degradation was identified, being this one resultant of the presence of Lewis acid in contact with this substance. Even though this mechanism covers any fluoroether compound presenting the radical —C—O—C—F, the sevoflurane demonstrate to be particularly susceptible to that kind of degradation.

Figure 1:
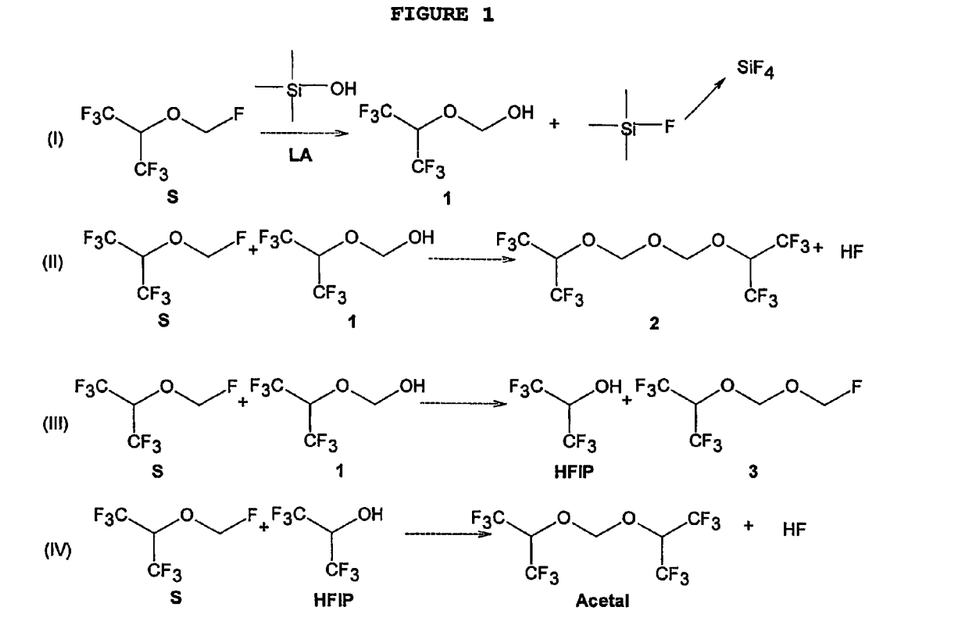
FIG. 1: Degradation scheme of sevoflurano (S) in the presence of Lewis acid (LA) bounded to the surface, with formation of the derivatives 1, 2, 3 and Acetal.

FIG. 1 presents the mechanism of degradation of sevoflurane (S) catalyzed by Lewis acid proposed on the document WO 98/32430. In that proposed mechanism, the degradation of sevoflurane is catalyzed by Lewis acids (LA) present in the composition of glass bottle used as package of sevoflurane.

Chemically the glass is constituted of silicates and contains a small amount of aluminum oxides among others substances. After its manufacture, glass undergoes treatment in order to inactivate its surface that means, there is not exposition of free hydroxyls bonded to the silica. However, the exposition of such hydroxyls can occur by occasion of presence of slots or wastage on the glass surface, which can be caused in any of the manufacture steps or during the asepsis of this material. These hydroxyls bounded to silica, if exposed, enter in contact with the sevoflurane leading to its degradation.

The complex mechanism of degradation of sevoflurane demonstrated in the FIG. 1 lead to the formation of toxic volatile substances, among them the hydrofluoric acid or other compound derived of its reaction with the glass, the $SiF_4$ (silicon tetrafluoride) being both extremely corrosive substances to the respiratory tract.

Figure 2:
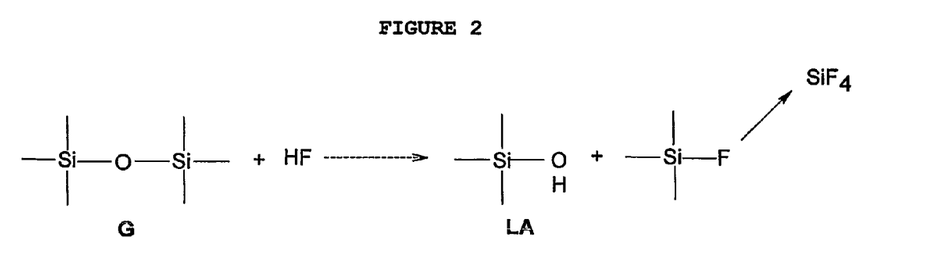
FIG. 2: Reaction scheme of hydrofluoric acid (HF) with the intact glass surface (V), exposing more Lewis acid on the surface (LA)

Further according to the mechanism demonstrated in the FIG. 1, it is possible to infer that it is a chain mechanism, where the degradation products, specially the hydrofluoric acid, degenerate the glass integrity (G) through the reaction demonstrated in the FIG. 2, exposing more Lewis acid on the surface (LA), which will react with a new molecule of sevoflurane restarting the degradation mechanism.

Among the inhalant anesthetics currently available, the sevoflurane presents the better index of acceptance by medical professionals and their patients. Since its launch at Japan in 1990, this anesthetic has been presenting crescent use due to its qualities over the others inhalant anesthetics, mainly its pleasant and non pungent odor and the faster induction and recovery of anesthesia in adults and child.

Since its launch, this product is marketed in glass packages, which are the packages of choice to several inhalant anesthetics. As the glass quality, referring to the presence of catalytic amount of Lewis acid bounded to surface is almost impossible to control, the development of a stabilized composition or method for stabilizing sevoflurane is of fundamental importance for viable marketing in this kind of package.

The classification of substances with property to act as Lewis acid is much extensive and broad. According to the Lewis theory, the acid corresponds to a species with an empty orbital able to accept an electron-pair forming a covalent bond. In summary, acid is a receptor of electron-pairs and base is a donator of electron-pairs [John B. Russel—*Quimica Geral*—1982 pg. 395]. Due to the coverage of materials which can be inserted in the classification of Lewis as acids, not only the glass represents a potential risk to sevoflurane stability, but also several others packages, containers or materials which the sevoflurane could be contact.

There are some references that treat about degradation of sevoflurane proposing solutions to eventual degradations caused by Lewis acids. It is the case, for example, of document WO 98/32430 that describes the use of Lewis acid inhibitors to avoid the degradation of sevoflurane. This patent describes the use of water to avoid the degradation of sevoflurane, which is employed in a concentration preferably ranging from 150 ppm to 1,400 ppm, that is, from 0.0150% to 0.1400% in weight related to sevoflurane. The experiments carried out employ high amounts of Lewis acid to demonstrate the inhibition of sevoflurane degradation by using water.

Although the document WO 98/32430 supposedly indicate an inhibition of sevoflurane degradation by water, actually that agent does not demonstrate to be efficient, even when employed in the recommended amounts to inhibition of sevoflurane degradation, as the proposed solution leads to HFIP (1,1,1,3,3,3-hexafluoroisopropanol) formation which leads to further degradation with formation of acetal (methyleneglycol bis-hexafluoroisopropyl ether) and hydrofluoric acid.

Other reference having the purpose of avoid the sevoflurane degradation is the U.S. Pat. No. 6,074,668 which proposes a container to sevoflurane storage. This container is made of material different from glass to avoid degradation by eventual presence of catalytic amounts of Lewis acid which lead to sevoflurane degradation according to above discussed mechanism. The container material is the polyethylene naftalate (PEN), which the authors suggest as most suitable than the glass by avoiding the sevoflurane degradation and the container break due to possible accidents in the surgical centers (surgery). The polyethylene naftalate is a material with plastic appearance considerably not permeable to that anesthetic and may be employed as a glass substitute to its storage. The main disadvantage of that kind of material as a package is its high price and the currently lack of ways to recycle it.

As few references in the literature propose a solution for the degradation problem of fluoroether compounds for anesthetic use, most particularly of sevoflurane, there is a need for the development of enough efficient ways to stabilize this compound and to control its degradation by acid substances.

Others references suggesting the use of packages from others materials, as the plastic materials, present some inconveniences as, for example, its permeability to volatile substances. Options in the area are the special plastic or polymeric materials as those described in U.S. Pat. No. 6,074,688 which in addition to the expensive price, they can not be recycled leading to polluted waste, contrary to the packages made of glass which are easily recycled consisting in an ecologically appropriated alternative. Other disadvantage of these materials is the possibility of acetaldehyde migration, substance produced during the package extrusion process due to material heat and also due to some mechanisms of degradation of packages containing polyethylene polymers.

The potential risk of sevoflurane contamination with acetaldehyde in packages of polyethylene naftalate (PEN) is described in the EMEA (The European Agency for the Evaluation of Medicinal Products) monograph of SevoFlo® product.

In addition to that inconveniences, these materials can also be classified as Lewis acid or can be contaminated during any manufacturing step or manipulation by Lewis acid, which can initiate the sevoflurane degradation mechanism when contact with it.

The solution described in the document WO 98/32430 proposing the water as inhibitor of degradation of sevoflurane didn't demonstrate capacity to assure appropriated inhibition of the degradation of that compound, since the observed formation of HFIP (1,1,1,3,3,3-hexafluoroisopropanol) is a convincible evidence that the mechanism is not inhibited enough to assure the non formation of the other degradation sub-product, that is, the hydrofluoric acid. In addition to that evidence which is supported by the self document, it is also known the sevoflurane degradation reported by Wallin et al. [R. F. Wallin, B. M. Regan, M. D. Napoli, I. J. Stern *Anesthesia and Analgesia* 1975, 54(6), 758], which describe that in water, the compound undergoes a slight but measurable hydrolysis. The formation of HFIP and the information referent to sevoflurane hydrolysis suggest that the water can also be involved in the mechanism of sevoflurane degradation, which make it an inappropriate substance as reliable inhibitor of degradation of this anesthetic agent.

In order to overcome all inconveniences of the prior art, the present invention describes a stable anesthetic composition comprising a fluoroether compound, such as sevoflurane, and an effective amount of at least one stabilizing agent selected from the group constituted of polyalcohols and saturated cyclic alcohols. Among the proper polyalcohols to be employed as stabilizing in the present invention are propylene glycol, polyethylene glycol, hexylene glycol and 1,3-butilenoglycol. Example of proper saturated cyclic alcohols to be employed in the present invention is menthol.

The compound sevoflurane (CAS 28523-86-6) is identified by the chemical name fluoromethyl 2,2,2-trifluoro-1-(trifluoromethyl)ethyl ether, whose molecular weight is 200.06, molecular formula is $C_4H_3F_7O$ and the structural formula can be observed in the FIG. 1 identified by letter S.

The propylene glycol is identified by the chemical name 1,2-propanediol (CAS 57-55-6).

The polyethylene glycol (CAS 25322-68-3) corresponds to a polymer of general formula $H(OCH_2CH_2)_nOH$, where n is equal or greater than 4. In general, each polyethylene glycol is followed by a number that corresponds to its average molecular weight.

The hexylene glycol is identified by the chemical name 2-methyl-2,4-pentanediol (CAS 107-41-5).

The 1,3-butileneglycol is identified by the chemical name 1,3-butanediol (CAS 107-88-0).

The menthol is identified by the chemical name (1 alpha, 2 beta, 5 alpha)-5-methyl-2-(1-methylethyl)cyclohexanol (CAS 89-78-1).

The pharmaceutical composition of the present invention can be prepared by adding an effective amount of stabilizing agent to the fluoroether compound such as sevoflurane or by adding the fluorether compound such as sevoflurane to the stabilizing agent to prevent the degradation of the fluorether compound such as sevoflurane by acid substances. Acid substances according to the present invention refer to substances of acid character, and in special, to metallic impurities of acid character, which in diverse conditions can contact with a fluoroether compound such as sevoflurane.

The present invention also describes a method for stabilizing a fluoroether compound, and most particularly a fluorether compound for anesthetic use such as sevoflurane, which consist in adding or placing in contact an effective amount of a stabilizing agent to the fluoroether compound such as sevoflurane in order to preclude its degradation. Among the appropriate stabilizers to be employed in the stabilization method proposed in the present invention, the polyalcohols and saturated cyclic alcohols are detached. Among the appropriated polyalcohols to be employed in the method of the present invention, particularly proposed for stabilizing sevoflurane, propylene glycol, polyethylene glycol, hexylene glycol, 1,3-butileneglycol or mixtures thereof are detached. Among the appropriated saturated cyclic alcohols to be employed in the present invention the menthol is detached.

According to the present invention, a fluoroether compound, such as the sevoflurane, can be stabilized by using substances as polyalcohols selected from a group constituted of propylene glycol, polyethylene glycol, 1,3-butileneglycol, hexylene glycol, or mixtures thereof and the saturated cyclic alcohols, among them the menthol. These substances completely prevent the formation of HFIP, HF and others degradation products of sevoflurane, being extremely efficient in protect the sevoflurane from reactive substances of acid character.

The present invention further describes an anesthetic composition comprising sevoflurane that doesn't degrade in the presence of acid substances due to addition of stabilizers substances as the polyalcohols and saturated cyclic alcohols. It also describes methods for preparing stable anesthetic composition of sevoflurane.

The pharmaceutical composition of the present invention comprises sevoflurane in any amount in weight in relation to the stabilizer agent. To be used as inhalation anesthetic, preferably the pharmaceutical composition comprises sevoflurane in a concentration ranging from 95% to 99.999% in weight of the final composition. The stabilizer agent added in the pharmaceutical composition of the present invention is a substance able to prevent the degradation of sevoflurane in presence of reactive substances having acid character. This stabilizer agent is selected from a group constituted of polyalcohols and saturated cyclic alcohols. Among the appropriate polyalcohols to be used as stabilizers in the present invention, propylene glycol, polyethylene glycol, hexylene glycol, 1,3-butileneglycol or mixtures thereof are detached. Among the appropriated saturated cyclic alcohols to be used in the present invention the menthol is detached.

The stabilizer agent for the fluoroether compound, and most particularly for the sevoflurane, is employed in concentration ranging from 0.001% in weight in relation to the weight of sevoflurane until its level of saturation in the sevoflurane, that is, the maximum concentration in which it keeps soluble in the sevoflurane. The amount of stabilizer agent to achieve its saturation depends on the stabilizer and temperature, and can be high due to the solubility profile among these substances. This is the case, for example, of polyethylene glycol 400 that is freely soluble in the sevoflurane. Generally, the stabilizer agents in the present invention are preferably used in amounts ranging from 0.001% to 5% in weight in relation to the weight of sevoflurane. However, higher amounts of stabilizer also make part of the present invention scope, since the stabilizer agents promote the stabilization of the substance target in any amount.

Among the appropriate polyalcohols to the stabilization of the fluoroether compound sevoflurane, propylene glycol, polyethylene glycol, hexylene glycol and 1,3-butileneglycol are chosen. These substances are appropriate pharmaceutical excipients to the use in pharmaceutical compositions and their toxicological data is well known. As cited before, the amount of the stabilizer agent will range from 0.001% in weight until its saturation level in sevoflurane. In the specific case of propylene glycol, its saturation level in the sevoflurane is around 2.5%, whereas the polyethylene glycol 400 is freely soluble in the sevoflurane. Therefore, in a general way, the polyalcohols are preferably employed in amounts ranging from 0.001% to 5.0% in weight in relation to the weight of sevoflurane.

Among the appropriate saturated cyclic alcohols to stabilization of sevoflurane, the preferential is menthol. This substance is an appropriate pharmaceutical excipient to the use in pharmaceutical compositions and its toxicological data is well known. As cited before, the amount of this stabilizer agent will range from 0.001% in weight until its saturation level in sevoflurane that is about 6.8%, being preferably employed in amounts ranging from 0.001% to 5.0% in weight in relation to the weight of sevoflurane.

The stabilizers agents used in the present invention demonstrate to be highly efficient in preclude the degradation of sevoflurane in any used amount. In inhalation anesthesia the purity of the anesthetic agent is particularly important as the presence of different substances in high amounts can lead to an undesirable action in the machine used to vaporization and administration of the anesthetic agent, such as deposit of residues in the circuit or even the necessity of special machine calibration to the vaporization condition of that product.

So, in a most preferred variant of the present invention, the amount of stabilizer agent used to preclude the degradation of sevoflurane by acid substances is in the range from 10 ppm to 2,000 ppm (from 0.001% to 0.200% in weight of stabilizer agent in relation to sevoflurane).

An important factor to be highlighted is referent to the behavior of the stabilizer substance in relation to its concentration, since depending on the inactivation type and concentration of degrading in the medium, its concentration in the final product can decrease during the storage period of the final product. The stabilizing agents act by eliminating or inactivating the harmful substance to the stability of the stabilized agent that, in the case of the present invention, is a fluoroether compound, such as sevoflurane. The stabilizer efficiency is directly correlated with its affinity by the degrading, this affinity must exceed several times the affinity of the substance to be stabilized by the same degrading.

The method for stabilizing sevoflurane of the present invention consists of adding or placing in contact an effective amount of a stabilizing agent to the sevoflurane in order to completely prevent the formation of HFIP and HF. Several procedures can be adapted to the proposed stabilization method, but are advantageous and preferable the practical procedures leading to formation of homogeneous mixtures and quantitatively established between stabilizing and sevoflurane. Among the appropriate stabilizing agents to be employed in the stabilization method proposed in the present invention, the polyalcohols and saturated cyclic alcohols are detached. Among the appropriate polyalcohols to be employed in the stabilization method of the present invention, propylene glycol, polyethylene glycol, hexylene glycol, 1,3-butileneglycol or mixtures thereof are detached. Among the appropriate saturated cyclic alcohols to be employed in the present invention, the menthol is detached.

In a general way, the stabilizer agent can be added to the sevoflurane in any step of its manufacture as, for example, in industrial packages of storage and transport of that product in great quantities, in the reservoir of the machine used to filling the finished pharmaceutical product, in the bottle of filling the final pharmaceutical composition, at last, in any step of sevoflurane manipulation.

Preferably, the stabilizing agent is added to sevoflurane previous to the product package, through quantitative measure apparatus, to assure addition of appropriate amount relative to the amount of sevoflurane to be stabilized, and formation of a homogeneous mixture.

Alternatively, according to the proposed method for stabilizing sevoflurane, the stabilizer agent is added to the storage recipient before its filling with sevoflurane.

To avoid previous exposition of non-stabilized fluoroether compound, such as sevoflurane, to surfaces that could present acid substances, the stabilization method of the present invention propose treat them with the stabilizing agent by diverse procedures in order to eliminate or inactivate eventual traces of acid substances. In a variant of the method, the stabilizer agent is placed in contact with the container or recipient as for example a bottle of glass, plastic, steel, or other material, by rinsing them with the stabilizer. Based on the physical characteristics of the stabilizer, it can be nebulized, vaporized or asperse on the internal surface of the bottle or recipient to the storage of sevoflurane, forming a film on that surface.

Most part of package materials consists of substances or mixture of substances having an acid character. When they don't contain such substances, they can contact them in any step of its manipulation. As the degradation of sevoflurane consist in a chain mechanism started only by the presence of a catalytic amount of an acid substance, its exposition to this kind of substance can be prejudicial to its stability. So, the present invention offers a solution for precluding the degradation of a fluoroether compound, such as sevoflurane, by acid substances, being its use adequate to any kind of package for storing sevoflurane.

As the presence of catalytic amounts of acid impurity substances can be prejudicial to sevoflurane, a safety measure is only using it containing the stabilizer agent. In this way, the present invention is, in other variant, employed to stabilize sevoflurane packed in packages not only of glass but also of plastic materials, steel, resins, polymers, at last, any material potentially having an acid impurities or that can had contacted with substances having an acid character during processing, storage, transport, asepsis, manipulation, etc.

The present invention demonstrates that substances as the polyalcohols and saturated cyclic alcohols have important properties and act in order to preclude the degradation of sevoflurane by acid substances, wherein the improvement, in relation to prior art proposing water as stabilizing, is precluding the formation of HFIP and HF and others degradation products of sevoflurane when in presence of acid substances.

The development achieved with the present invention introduce a new class of substances which present stabilizing properties for compounds as sevoflurane and others similar fluoroether compounds which are capable of suffering the same deleterious action when in contact with substances having acid character.

The comparative studies showed in the examples of this document demonstrate the ability of the compounds described in the present invention in prevent the degradation of the fluoroether compound sevoflurane, being the prevention provided by them most effective than that provided by the water such as that one described in the document WO 98/32430.

Also according to the studies showed in the examples, preferably directed to the fluoroether compound sevoflurane, it is verified that the present invention is not limited to stabilization of anhydrous sevoflurane.

Results of analyses where sample of "sevoflurane containing water as stabilizing agent" is exposed to a substance having acid character as alumina demonstrate that the stabilization is not effective since it is verified sample degradation with formation of HFIP and increasing of fluorides content, indicating the low potential of stabilization of water.

Wet samples containing the stabilizers of the present invention don't degraded, indicating the high potential of stabilization of theses substances.

As cited before, sevoflurane in water undergoes a slight and measurable hydrolysis that was evidenced by the studies showed in the examples. The compounds of the present invention completely prevent that degradation since the HFIP and fluorides contents don't increase.

According to the present invention the compounds proposed to stabilization of sevoflurane are also efficient in stabilize the sevoflurane with water content superior to 20 ppm, being efficient stabilizers when used in the wet sevoflurane presenting water content of until its saturation level of about 1400 ppm (0.14%).

The present invention has an unlimited scope in order to provide an effective stabilization of sevoflurane and fluoroethers compounds with similar chemical characteristics, being not only applicable to compositions but also to different solutions in which the sevoflurane or the fluoroether compound could be manufactured or stored.

Following there is a brief description of the figures cited in this document.

The present invention will be described in detail by the following illustrative examples, but not exhausting ones, of the several applications and possibilities which comprise or derivate of the present invention. Although the composition and method of the following examples are described in relation to its preferred variants, it will be evident to persons skilled in the art that several changes can be made without deviate from the present invention scope.

EXAMPLES

In the following examples, all analyses by gas chromatography were carried out by adding 2 µL of toluene (internal standard) in 10 mL of sample of sevoflurane in study. The analysis was done in duplicates and for each chromatogram obtained was calculated the ratio of the area of each impurity/area of toluene. The values showed in the tables represent the average ratio obtained from the duplicate chromatographic analysis.

Example 1

Degradation of Sevoflurane by Acid Substances

This introductory study had as objective select the stress conditions to be used in the following studies employing stabilizer substances.

The degradation of sevoflurane by acid substances can be observed, for example, when a sample of anhydrous sevoflurane is placed in contact with alumina ($Al_2O_3$) and undergoes heating at 60° C. for 22 hours.

Figure 3:
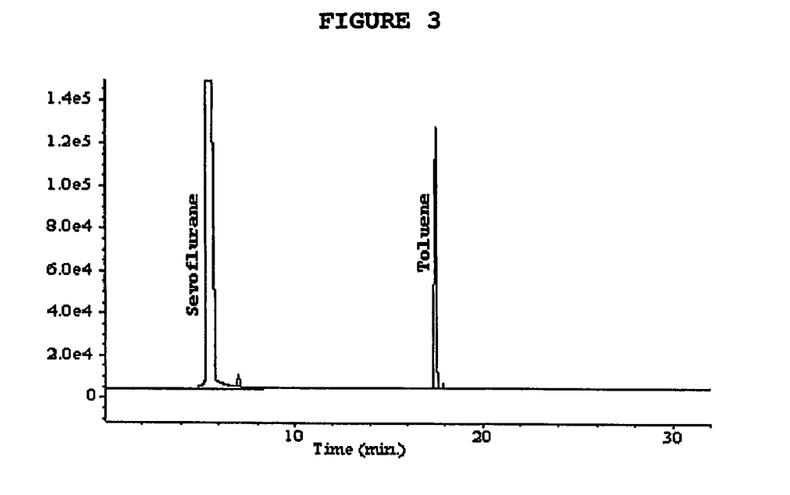
FIG. 3: Chromatogram of anhydrous sevoflurane (water content=20 ppm) after heating at 60° C. for 22 hours in the absence of alumina.
Figure 4:
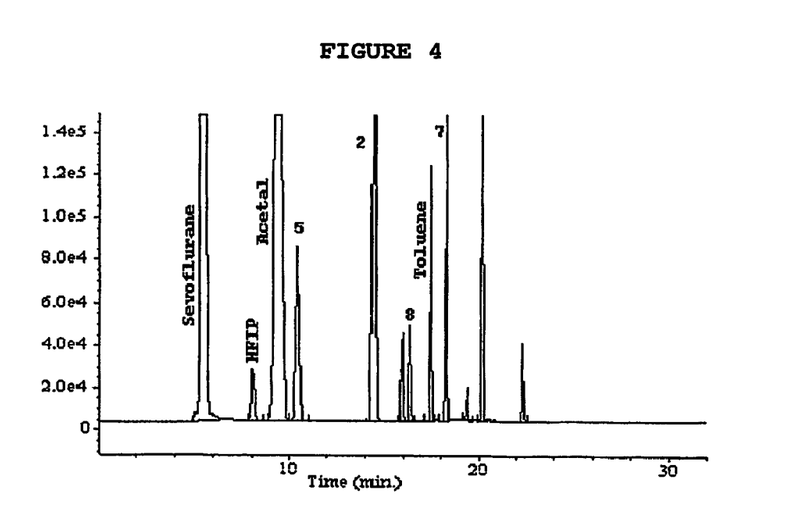
FIG. 4: Chromatogram of anhydrous sevoflurane (water content=20 ppm) after heating at 60° C. for 22 hours in the presence of 1 mg of alumina per milliliter of sevoflurane.

The sevoflurane used in the tests was previously dry with molecular sieve reaching the water content of 20 ppm. In two type III glass bottle with capacity of 100 mL, was added 20 mL of anhydrous sevoflurane and in one of the bottles was added 20 mg of alumina totalizing 1.0 mg of $Al_2O_3$ per mL of sevoflurane. Both bottles were closed with a stopper and screw metallic cap and heated in a stove at 60° C. for 22 hours. After that period, the samples were analyzed in duplicates by gas chromatography using the internal standard addition method (toluene). FIG. 3 shows the chromatogram of anhydrous sevoflurane sample heated without alumina, condition in which degradation is not observed. The degradation products of sevoflurane monitored by gas chromatography, HFIP, Acetal, 2, 5, 7 and 8, are present in high amounts in the samples of sevoflurane containing alumina after heating, as presented in FIG. 4.

Figure 5:
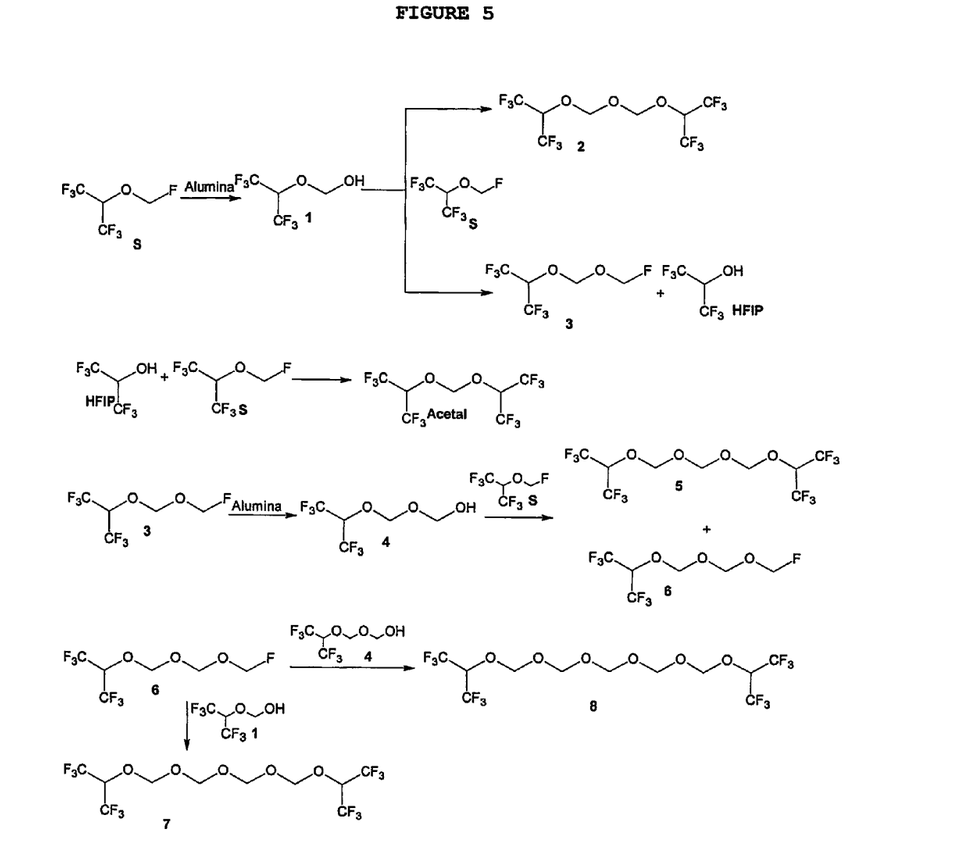
FIG. 5: Degradation scheme of sevoflurane in presence of alumina.

FIG. 5 shows the degradation scheme of sevoflurane under action of alumina indicating the impurities observed and monitored.

As the amount used of activated alumina was enough to provoke a significant degradation of sevoflurane, such amount was used in the studies to select the stabilizer agents for sevoflurane.

Example 2

Influence of Water on the Sevoflurane Stability

This example shows the investigation about the influence of water on the sevoflurane stability. According to the document WO 98/32430, a water content of 150 ppm to 1400 ppm present in sevoflurane would assure its stabilization inhibiting the formation of degradation products.

The study was carried out using sevoflurane dried with molecular sieve to reach initial water content of 20 ppm. The protection or degradation degree of sevoflurane, when in contact to alumina in presence of water, was evaluated from samples of sevoflurane containing different water content treated or not with alumina in the proportion of 1 mg per mL of sevoflurane. The samples were prepared and placed in type III glass bottle and the bottles were closed with stopper and screw metallic cap.

The samples were submitted to two stress conditions by heating in stove at 60° C. for a cycle of 22 hours and other of 72 hours.

TABLE 1

| Study Conditions | Water/ppm | Total Impurity[1] | | HFIP[2] | |
|---|---|---|---|---|---|
| | | 0 mg of $Al_2O_3$ | 20 mg of $Al_2O_3$ | 0 mg of $Al_2O_3$ | 20 mg of $Al_2O_3$ |
| 60° C. for 22 hours | 0 | 0.2373 | 33.1675 | 0.0018 | 0.6613 |
| | 260 | 0.3574 | 1.6294 | 0.0039 | 0.5925 |
| | 600 | 0.3089 | 0.3315 | 0.0014 | 0.0189 |
| | 1000 | 0.3221 | 0.3598 | 0.0035 | 0.0199 |
| 60° C. for 72 hours | 0 | 0.4281 | 41.110 | 0.000 | 1.2334 |
| | 100 | 0.3901 | 50.1053 | 0.000 | 1.2075 |
| | 260 | 0.4063 | 30.5679 | 0.000 | 1.7817 |

[1]Average sum of the ratios area of each impurity/area of toluene (internal standard);
[2]Average of the ratios area of HFIP/area of toluene.

In agreement with the tabled results in the presence of water and alumina the values for total impurity and HFIP varied considerable as a function of the study. Despite of the results indicate an inhibition of the degradation of sevoflurane by alumina starting only with 600 ppm of water, they also indicate that the values obtained for HFIP remaining relatively elevated.

Figure 6:
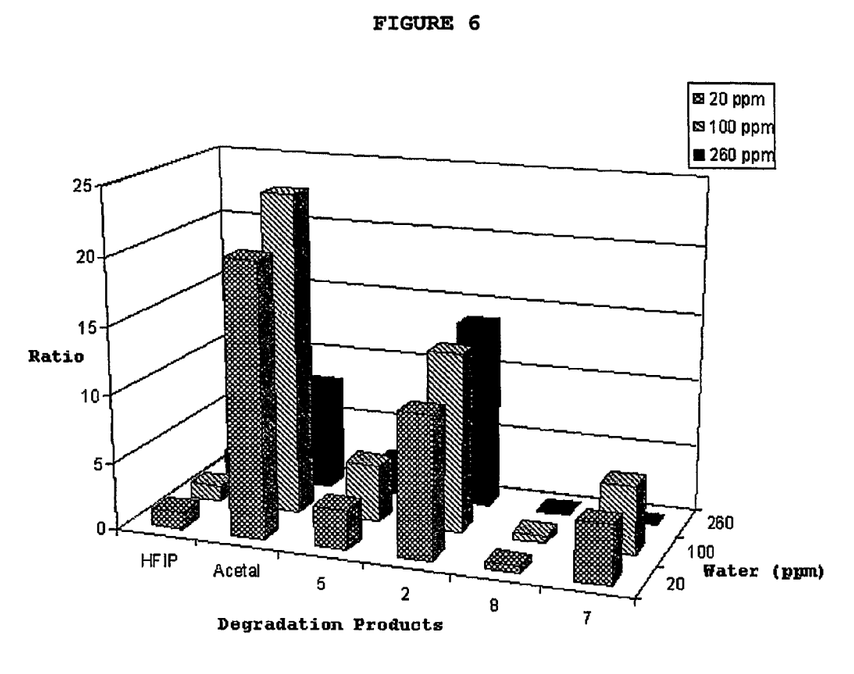
FIG. 6: Water effect in the stabilization of sevoflurane relating to the degradation by alumina (1 mg per milliliter of sevoflurane), after sample heating at 60° C. for 72 hours.

FIG. 6 shows the evolution of the mean products of degradation of sevoflurane in the greater stress conditions. In agreement with the results was observed a higher degradation of sevoflurane in the samples containing 100 ppm of water than in the sample containing 20 ppm of water, which indicates that the water may be important for the occurrence of degradation of sevoflurane participating in the degradation mechanism of this substance in an acid condition, not being only a stabilizer as described in patent WO 98/32430. It is obviously that the decomposition of sevoflurane was inhibited by higher concentrations of water as generally occur for many organic reactions. Meanwhile, as described by Wallin et al. [R. F. Wallin, B. M. Regan, M. D. Napoli, I. J. Stern *Anesthesia and Analgesia* 1975, 54 (6), 758] sevoflurane in water suffered a slow but measurable hydrolyses, which is an evidence supporting the hypothesis that the water may be evolved in some mechanism which promotes the degradation of sevoflurane and this was observed by the results obtained in the present study.

Example 3

Stabilization of Sevoflurane Against the Degradation by Alumina with the Addition of a Polyalcohol or a Saturated Cyclic Alcohol In this example the prevention of the degradation of sevoflurane by alumina is effected by employing a polyalcohol and a saturated cyclic alcohol. The substances selected in each group were propylene glycol and menthol, respectively.

The sample was prepared to contain 0, 50, 200, 600, 1000 and 1400 ppm of the stabilizer agent. The sevoflurane employed to prepare these samples was previously dried with molecular sieves to achieve the quantity of 20 ppm of water. The study comprises put sevoflurane in contact with an acid substance, submits the samples to a stress by heating at 60° C. for 22 hours and, by comparison evaluates the chromatographic purity of sevoflurane after stress. The activated alumina was employed as acid substance in a constant quantity of 1 mg per mL of sevoflurane.

In type III glass bottle with capacity for 100 mL was transferred 20 mL of test sevoflurane containing determined quantities of the stabilizer agent (0, 50, 200, 600, 1000 and 1400 ppm) and 20 mg of alumina. The bottles were immediately closed with a stopper and a screw metallic cap. These bottles were heated in a stove at 60° C. for 22 hours. After the stress the samples were analyzed in duplicate by gas chromatography using the internal standard addition method (toluene). In parallel, studies were done with the quantity determined of the stabilizer (0, 50, 200, 600, 1000 and 1400 ppm) without alumina.

Table 2 resumes the tests realized with the agents propylene glycol and menthol proposed for the stabilization of sevoflurane against the degradation by alumina and the results for total impurity and for the single impurity HFIP obtained with and without alumina after stress at 60° C. for 22 hours. The total impurity is the sum of the ratio between the area for each impurity and the area of the internal standard (toluene) and HFIP is the ratio between the area of HFIP and the area of toluene obtained in the chromatograms.

TABLE 2

| Stabilizer | Concentration (ppm) | Total Impurity[1] | | HFIP[2] | |
|---|---|---|---|---|---|
| | | 0 mg of $Al_2O_3$ | 20 mg of $Al_2O_3$ | 0 mg of $Al_2O_3$ | 20 mg of $Al_2O_3$ |
| PROPYLENE GLYCOL | 0 | 0.3304 | 31.65325 | 0.04910 | 0.6680 |
| | 50 | 0.3293 | 0.3925 | 0 | 0.05996 |
| | 200 | 0.3546 | 0.2823 | 0.04474 | 0.04072 |
| | 600 | 0.2925 | 0.3158 | 0.04694 | 0.04603 |
| | 1000 | 0.3800 | 0.3189 | 0.04038 | 0.04353 |
| | 1400 | 0.3061 | 0.3235 | 0.04159 | 0.04236 |
| MENTHOL | 0 | 0.3083 | 37.5478 | 0.04080 | 0.8914 |
| | 50 | 0.3174 | 1.0412 | 0.04541 | 0.6402 |
| | 200 | 0.2918 | 1.0773 | 0.04228 | 0.5880 |
| | 600 | 0.3319 | 1.0001 | 0.04445 | 0.4426 |
| | 1000 | 0.3627 | 0.9486 | 0.04669 | 0.3787 |
| | 1400 | 0.3644 | 1.0156 | 0.04325 | 0.3329 |

[1] Average sum of the ratios area of each impurity/area of toluene (internal standard);
[2] Average of the ratios area of HFIP/area of toluene.

Figure 7:
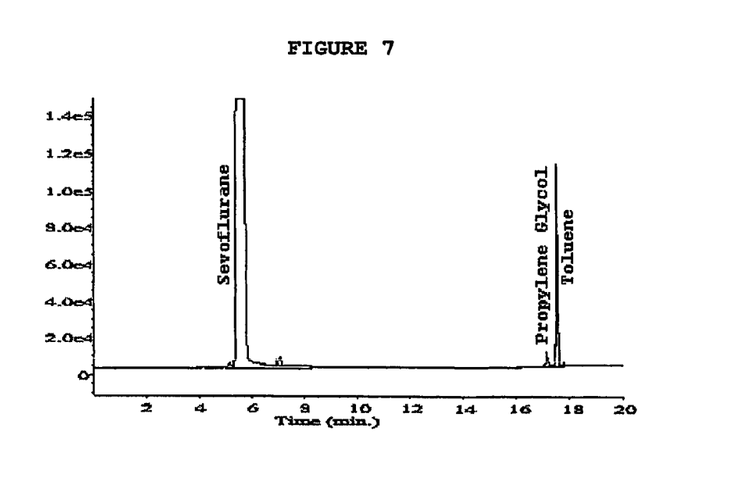
FIG. 7: Chromatogram of anhydrous sevoflurane containing 50 ppm of propylene glycol after heating at 60° C. for 22 hours in the presence of 1 mg of alumina per milliliter of sevoflurane.

The results of Table 2 show that without alumina, the values of the average total impurity for the samples containing different concentration of the stabilizer agents remain very near to the values obtained without the stabilizer. In the presence of alumina, the high value of the average total impurity observed for sevoflurane without stabilizer is significantly reduced in the samples containing propylene glycol or menthol as a stabilizer. FIG. 7 shows that sevoflurane with 50 ppm of propylene glycol didn't degrade in the presence of alumina after stress at 60° for 22 hours and, when compared with example 2, it demonstrates to be a superior stabilizer than water.

Example 3.1

Figure 8:
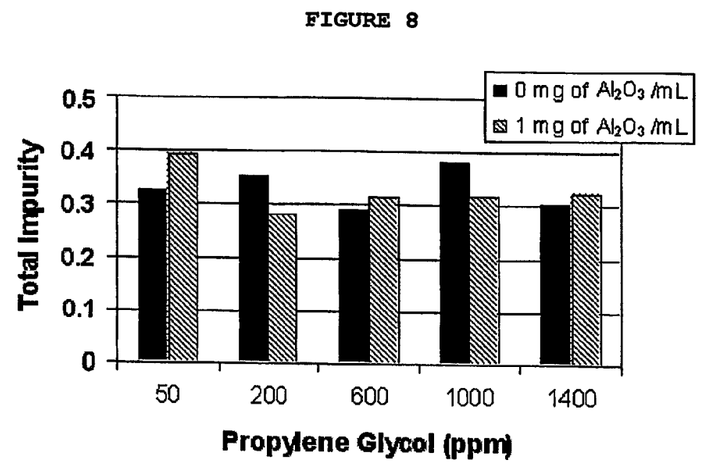
FIG. 8: Effect of propylene glycol in the stabilization of sevoflurane relating to the degradation by alumina (1 mg per milliliter of sevoflurane), after sample heating at 60° C. for 22 hours.

Total Impurity Evolution of Sevoflurane as Function of the Concentration of the Stabilizer FIG. 8 shows a bar graphic comparing the average total impurity of sevoflurane after stress at 60° C. for 22 hours as function of the concentration of propylene glycol with or without 1 mg of alumina per mL. This figure demonstrates the effective stabilization of sevoflurane by propylene glycol against the degradation by alumina already in concentration as small as 50 ppm and for all the studied concentrations of propylene glycol.

The average total impurity for the samples containing propylene glycol didn't change with or without alumina demonstrating its very efficient stabilization of sevoflurane.

Menthol also is efficient in the stabilization of sevoflurano against the degradation by alumina and the stabilization effect is practically independent on its concentration, Table 2. Despite the average total impurity of sevoflurane with menthol is little superior to the values obtained without alumina and in the samples with propylene glycol, is possible to observe that the stabilization provided by menthol is as or more efficient as the observed with water, Table 1.

Example 3.2

Figure 9:
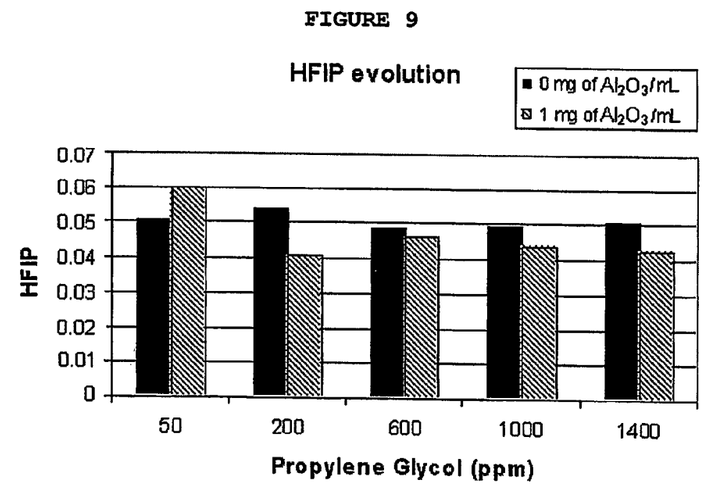
FIG. 9: Effect of propylene glycol in the stabilization of HFIP impurity content relating to degradation by alumina (1 mg per milliliter of sevoflurane), after sample heating at 60° C. for 22 hours.

Evolution of the Impurity HFIP as Function of the Concentration of the Stabilizer FIG. 9 demonstrates that 50 ppm of propylene glycol is sufficient to prevent the degradation of sevoflurane and the consequent formation of HFIP differently from the observed with water which was not able to completely inhibit the degradation of sevoflurane in the presence of alumina even in a concentration of 260 ppm, with the sample showing a higher value for HFIP than that observed for the sample without alumina (Table 1).

The apparent inhibition provided by water is relative, as the impurity HFIP value increases about 10 times in relation to the sample without alumina, attesting the degradation of sevoflurane. This isn't observed with propylene glycol whose values of HFIP remaining unchangeable in the presence or absence of alumina.

Figure 10:
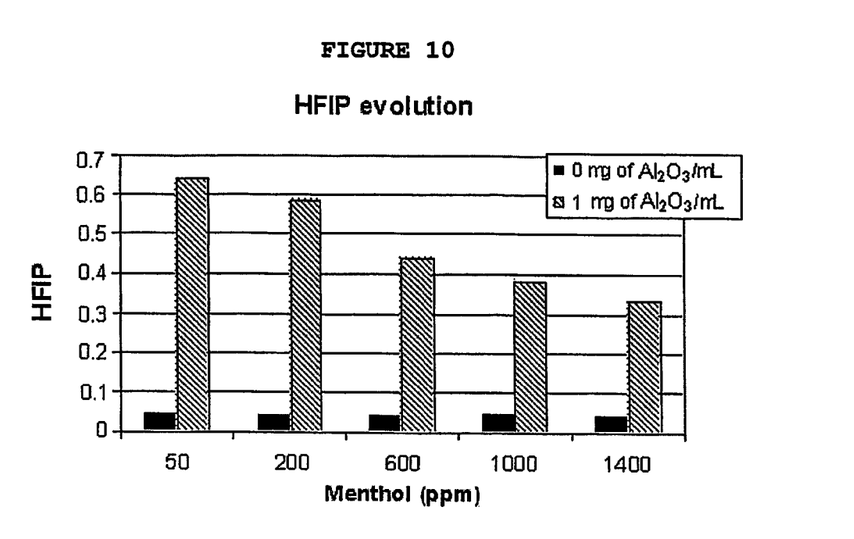
FIG. 10: Effect of menthol in the stabilization of the HFIP impurity content relating to degradation by alumina (1 mg per milliliter of sevoflurane), after sample heating at 60° C. for 22 hours.

In the case of sevoflurane containing menthol, FIG. 10 shows that the impurity HFIP diminishes as the menthol concentration increases.

The results of total and single impurity (example 3.1 and 3.2, respectively) for propylene glycol show its adequate stabilization effect against the degradation by alumina mainly keeping unchangeable the impurity results in the presence of alumina in relation to the results without alumina.

The results show that propylene glycol can be considered a better stabilizer than water therefore completely prevents the degradation of sevoflurane by an acid substance and mainly prevents the formation of HFIP which is one of the first products of degradation of sevoflurane.

Example 4

Comparison of the Effect of Different Stabilizers Added to Sevoflurane

The present study compares the effects of stabilization of sevoflurane proportionate by water, propylene glycol and polietilene glycol, all employed in a concentration of 50 ppm.

Table 3 show the results, after stress at 60° C. for 12 hours, for total impurity and for a single impurity (HFIP) of samples of sevoflurane containing 50 ppm of the stabilizer agents water, propylene glycol and polyethylene glycol with and without alumina.

TABLE 3

| Stabilizer (ppm) | Total Impurity[1] | | HFIP[2] | |
|---|---|---|---|---|
| | 0 mg of $Al_2O_3$ | 20 mg of $Al_2O_3$ | 0 mg of $Al_2O_3$ | 20 mg of $Al_2O_3$ |
| Water 50 | 0.33504 | 12.09169 | 0.00206 | 0.82027 |
| Propylene glycol 50 | 0.32365 | 0.39628 | 0.00338 | 0.02051 |
| PEG 400 50 | 0.34048 | 0.36273 | 0.00122 | 0.01717 |

[1] Average sum of the ratios area of each impurity/area of toluene (internal standard);
[2] Average of the ratios area of HFIP/area of toluene.

Figure 11:
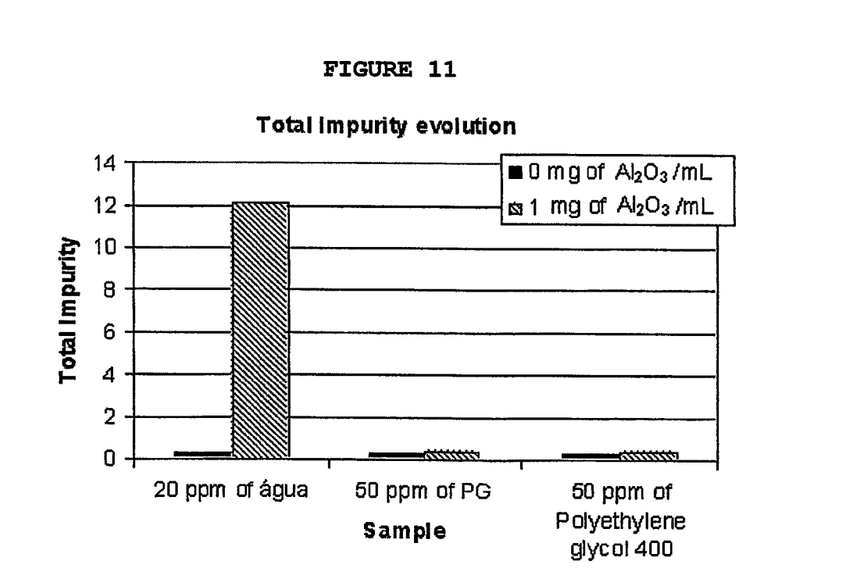
FIG. 11: Comparison of average total impurity value of anhydrous sevoflurane (about 20 ppm of water) containing 50 ppm of propylene glycol or 50 ppm of PEG 400, in the absence or in the presence of 1 mg of alumina per milliliter of sevoflurane, after samples heating at 60° C. for 22 hours.

FIG. 11 shows a bar graphic comparing the effects of the stabilizers in the total impurity constructed with the results of table 3. Complete prevention of the degradation of sevoflurane catalyzed by alumina was observed with polyalcohols like propylene glycol and PEG 400. PEG 400, likes propylene glycol, completely prevents the formation of HFIP unlike water which was incapable to inhibit the formation of HFIP even in the concentration of 260 ppm.

Figure 12:
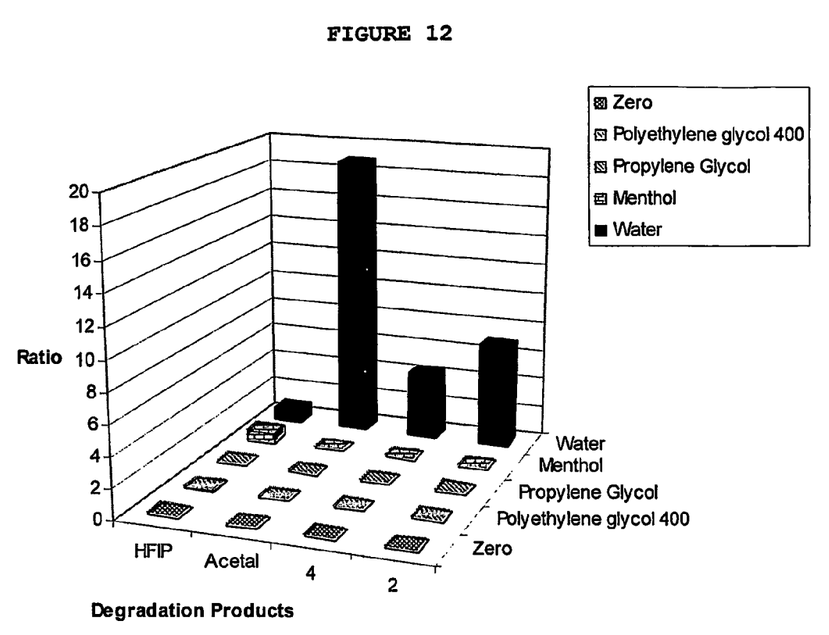
FIG. 12: Comparison of degradation products of sevoflurane containing 50 ppm of water, propylene glycol, PEG 400, or menthol, after samples heating at 60° C. for 22 hours in the presence of 1 mg of alumina per milliliter of sevoflurane, in relation to "zero" that corresponds to the result obtained to the sample of sevoflurane containing 50 ppm of water after heating to 60° C. for 22 hours in the absence of alumina.

FIG. 12 shows a bar graphic showing the evolution of the principal products of the degradation of sevoflurane as function of the stabilizer in a fixed quantity of 50 ppm, constructed with the results of table 2 (menthol) and table 3 (water, propylene glycol or PEG 400. In the samples containing 50 ppm of water was observed degradation with formation of HFIP, acetal, 2 and 5, while in the sample containing propylene glycol or PEG 400 the degradation catalyzed by alumina is completely precluded. The water is incapable to completely inhibit the degradation of sevoflurane by alumina leading to increases of the impurities HFIP and acetal, detected in all analysis, which contribute in large scale for the average total impurity results.

Example 5

Stabilization of Sevoflurane Against Degradation by Alumina. Impurities, Assay and Limit of Fluoride In this study alumina was employed in a final concentration of 1 mg per mL of sevoflurane. The samples of sevoflurane were prepared to present 260 ppm of water or 260 ppm of propylene glycol, in type III amber glass bottles which were closed with a plastic stopper and a screw metallic cap, and then stressed at 60° C. for 22 hours.

Table 4 shows the results of gas chromatographic analysis of the samples containing 260 ppm of water or propylene glycol after stress. The complete preclusion of the degradation of sevoflurane was observed with propylene glycol and the product containing propylene glycol accomplishes the specifications of single and total impurity. Nevertheless, 260 ppm of water didn't inhibit the degradation of sevoflurane by alumina and the product containing water after the stress didn't accomplish the specification of single and total impurity.

TABLE 4

| | | | Sevoflurane containing stabilizer | |
|---|---|---|---|---|
| Assay | Specification[1] | Anhydrous Sevoflurane[2] | Water (260 ppm) | PG[3] (260 ppm) |
| Purity | Min. 99.97% | 99.9798 | 99.8944 | 99.9774 |
| Compound A | Max. 25 µg/g | 11.2 | 11.8 | 11.3 |
| Single impurity | Max. 100 µg/g | 63.7 | 403 | 61.7 |
| Total Impurity | Max. 300 µg/g | 201.8 | 1056.1 | 226.3 |

[1]Pharmacopeial Forum USP Vol. 27 n°3;
[2]Initial analysis results of anhydrous sevoflurane employed in the preparation of the samples containing stabilizers;
[3]PG = propylene glycol.

The degradation observed for the sample containing 260 ppm of water in the presence of alumina is elevated and the sample didn't accomplish with the Pharmacopeial Forum USP, referent to the analysis of chromatographic purity and assay.

Another important factor observed in the present study is the quantity of fluoride in the sample submitted to stress. Table 5 shows the results for the anhydrous sevoflurane employed in the tests and the results for the samples submitted to the stress conditions:

TABLE 5

| | | | Sevoflurane with stabilizer | |
|---|---|---|---|---|
| Test | Specification[1] | Anhydrous Sevoflurane[2] | Water (260 ppm) | PG[3] (260 ppm) |
| Limit of fluoride | Max. 2 µg/mL | 0.050 µg/mL | 16.950 µg/mL | 0.051 µg/mL |

[1]Pharmacopeial Forum USP Vol. 27 n°3;
[2]Initial analysis results of anhydrous sevoflurane employed in the preparation of the samples containing stabilizers;
[3]PG = propylene glycol.

In agree with Table 5 the analysis of quantification of fluoride presents high result for the sample with water as the stabilizer. In this stressed sample the quantity of fluoride is 339 times higher than the original sample analyzed before the stress and 8 times higher than maximum limit established by the method, which prove its dangerous degradation and the inefficacious of water as inhibitor of the degradation of sevoflurane. Differently, the sample of sevoflurane with 260 ppm of propylene glycol didn't show any degradation in the presence of alumina and accomplish the specifications described in the Pharmacopeial Forum vol 27 n°3, including the content of fluoride which didn't present variation comparing with the original sample.

Example 6

Stabilization of Wet Sevoflurane by Employing Polyalcohols

This study illustrate the stabilization power of a polyalcohol in preclude the degradation of wet sevoflurane. In the example 5 was verified accentuated degradation of sevoflurane having water as the stabilizer agent. The purpose of this study is to demonstrate the stabilization of humid sevoflurane by a polyalcohol, for example, propylene glycol, to prevent the degradation of sevoflurane by acid substance.

Alumina was employed in a final concentration of 1 mg per mL of sevoflurane. The samples of sevoflurane were prepared to present 260 ppm of water or a mixture of 260 ppm of water and 260 ppm of propylene glycol, in type III amber glass bottles which were closed with a plastic stopper and a screw metallic cap, and then stressed at 60° C. for 22 hours.

This study is done to verify the stabilization power of propylene glycol against the degradation observed in wet samples of sevoflurane.

The results of gas chromatographic analyses and limit of fluoride for the samples are displayed in Table 6:

TABLE 6

| | | | Stabilizer | |
|---|---|---|---|---|
| Test | Specifications[1] | Anhydrous sevoflurane[2] | Water (260 ppm) | PG[3] + water (260:260 ppm) |
| Purity | Min. 99.97(%) | 99.9907 | 99.8899 | 99.9874 |
| Single impurity | Max. 100 (µg/g) | 42.1 | 422.8 | 44.1 |
| Total impurities | Max. 300 (µg/g) | 93.0 | 1101.3 | 125.6 |
| Limit of Fluoride | Max. 2 µg/ml | 0.072 | 15.340 | 0.153 |

[1]Pharmacopeial Forum USP Vol. 27 n°3;
[2]Initial analysis results of anhydrous sevoflurane employed in the preparation of the samples containing stabilizers;
[3]PG = propylene glycol.

According to the earlier study, the protection provided by water against the degradation of sevoflurane by alumina was inadequate when water was employed in 260 ppm.

In the present study, we can ratify not only the efficiency of propylene glycol to provide an effective protection against the degradation of anhydrous sevoflurane catalyzed by acid substance but also the effective protection of wet sevoflurane, showing the non interference of water in its stabilization power.

The studies here showed to demonstrate the present invention efficacy, are only illustrative and not limitative of the present invention scope, which applies to the different kinds of fluoroether compounds used as anesthetic, such as earlier indicated in the specification.

We claim:

1. A stable pharmaceutical composition comprising a fluoroether anesthetic compound selected from the group consisting of sevoflurane, desflurane, isoflurane, enflurane and methoxyflurane, and at least one stabilizer agent employed in a concentration ranging from 0.001% to 0.200% in weight of the final composition, the stabilizer agent being selected from the group consisting of a polyalcohol selected from the group constituted of propylene glycol, polyethylene glycol, hexylene glycol 1,3-butyleneglycol, menthol, and mixtures thereof.

2. A stable anesthetic pharmaceutical composition comprising sevoflurane and at least one stabilizer agent, employed in a concentration ranging from 0.001% to 0.200% in weight of the final composition, the stabilizer agent being selected from the group consisting of a polyalcohol selected from the group consisting of propylene glycol, polyethylene glycol, hexylene glycol 1,3-butyleneglycol, menthol, and mixtures thereof.

3. The stable anesthetic pharmaceutical composition according to claim 2 wherein the stabilizing agent is propylene glycol employed in a concentration ranging from 0.001% to 0.200% in weight of the final composition.

4. The stable anesthetic pharmaceutical composition according to claim 2 wherein the stabilizer agent is a polyethylene glycol of general formula $H(OCH_2CH_2)_nOH$ where n is equal or greater than 4 employed in a concentration ranging from 0.001% to 0.200% in weight of the final composition.

5. The stable anesthetic pharmaceutical composition according to claim 4 wherein the stabilizer agent is polyethylene glycol 400.

6. The stable anesthetic pharmaceutical composition according to claim 2 wherein the stabilizing agent is menthol employed in a concentration ranging from 0.001% to 0.200% in weight of the final composition.

7. A stable anesthetic pharmaceutical composition comprising an amount of sevoflurane and propylene glycol in a concentration ranging from 0.005% to 0.100% in weight of the final composition.

8. A stable anesthetic pharmaceutical composition comprising an amount of sevoflurane and polyethylene glycol 400 in a concentration ranging from 0.005% to 0.100% in weight of the final composition.

9. A stable anesthetic pharmaceutical composition comprising an amount of sevoflurane and menthol in a concentration ranging from 0.005% to 0.100% in weight of the final composition.

10. A method for stabilizing sevoflurane comprising mixing sevoflurane with at least one stabilizer agent in a concentration ranging from 0.001% to 0.200% in weight in relation to the weight of sevoflurane, the stabilizer agent being selected from the group consisting of a polyalcohol selected from the group consisting of propylene glycol, polyethylene glycol, hexyleneglycol 1,3-butyleneglycol, menthol, and mixtures thereof.

11. The method according to claim 10 wherein the stabilizer agent is propylene glycol employed in a concentration ranging from 0.001% to 0.200% in weight in relation to the weight of sevoflurane.

12. The method according to claim 10 wherein the stabilizer agent is a polyethylene glycol of general formula $H(OCH_2CH_2)_nOH$ where n is equal or greater than 4 employed in a concentration ranging from 0.001% to 0.200% in weight in relation to the weight of sevoflurane.

13. The method according to claim 12 wherein the stabilizer agent is polyethylene glycol 400.

14. The method according to claim 10 wherein the stabilizer agent is menthol employed in a concentration ranging from 0.001% to 0.200% in weight in relation to the weight of sevoflurane.

15. A method for stabilizing anhydrous fluoroether anesthetic compounds comprising mixing the anhydrous fluoroether compound with at least one stabilizer agent employed in a concentration ranging from 0.001% to 5% in weight in relation to the weight of the fluoroether compound, the stabilizer agent being selected from the group consisting of a polyalcohol selected from the group consisting of propylene glycol, polyethylene glycol, hexylene glycol 1,3-butyleneglycol, menthol, and mixtures thereof.

16. The method according to claim 15 wherein the stabilizer agent is propylene glycol employed in a concentration ranging from 0.001% to 0.200% in weight in relation to the fluoroether compound.

17. The method according to claim 15 wherein the stabilizer agent is a polyethylene glycol of general formula $H(OCH_2CH_2)_nOH$ where n is equal or greater than 4.

18. The method according to claim 17 wherein the stabilizer agent is polyethylene glycol 400.

19. The method according to claim 18 wherein polyethylene glycol 400 is employed in a concentration ranging from 0.001% to 0.200% in weight in relation to the fluoroether compound.

20. The method according to claim 15 wherein the stabilizer agent is menthol employed in a concentration ranging from 0.001% to 0.200% in weight in relation to the fluoroether compound.

21. The method according to claim 15 wherein the anhydrous fluoroether compound is sevoflurane.

22. A method for stabilizing a wet fluoroether anesthetic compound having water content from 0.002% to 0.14% comprising mixing the wet fluoroether compound with at least one stabilizer agent employed in a concentration ranging from 0.001% to 5% in weight in relation to the fluoroether compound, the stabilizer agent being selected from the group consisting of a polyalcohol selected from the group consisting of propylene glycol, polyethylene glycol, hexylene glycol 1,3-butyleneglycol, menthol, and mixtures thereof.

23. The method according to claim 22 wherein the stabilizer agent is propylene glycol employed in a concentration ranging from 0.001% to 0.200% in weight in relation to the fluoroether compound.

24. The method according to claim 22 wherein the stabilizer agent is a polyethylene glycol of general formula $H(OCH_2CH_2)_nOH$ where n is equal or greater than 4.

25. The method according to claim 24 wherein the stabilizer agent is polyethylene glycol 400 employed in a concentration ranging from 0.001% to 0.200% in weight in relation to the fluoroether compound.

26. The method according to claim 22 wherein the stabilizer agent is menthol employed in a concentration ranging from 0.001% to 0.200% in weight in relation to the fluoroether compound.

27. The method according to claim 22 wherein the fluoroether compound having water content ranging from 0.002% to 0.14% is sevoflurane.

* * * * *